United States Patent [19]

von Berg

[11] Patent Number: 4,901,735

[45] Date of Patent: Feb. 20, 1990

[54] PRESSURE METER CATHETER WITH IN-SITU ZERO SETTING

[75] Inventor: Peter von Berg, Neukeferloh, Fed. Rep. of Germany

[73] Assignee: Peter von Berg Extrakorporale Systeme - Medizintechnik GmbH, Kirchessnon/Eglharting, Fed. Rep. of Germany

[21] Appl. No.: 260,055

[22] Filed: Oct. 20, 1988

[30] Foreign Application Priority Data

Oct. 4, 1988 [DE] Fed. Rep. of Germany ....... 3833723

[51] Int. Cl.⁴ .............................................. A61B 5/00
[52] U.S. Cl. .................................... 128/748; 128/673; 73/4 R
[58] Field of Search ............................... 128/672–675, 128/748, 664–667, 774; 73/4 R, 753, 756

[56] References Cited

U.S. PATENT DOCUMENTS 3,703,099 11/1972 Rouse .................................. 128/673
4,175,566 11/1979 Millar .
4,274,423  6/1981 Mizuno et al. ...................... 128/675
4,672,974  6/1987 Lee ..................................... 128/673
4,712,566 12/1987 Hok ................................ 128/673 X Primary Examiner—Angela D. Sykes
Attorney, Agent, or Firm—Cushman, Darby & Cushman

[57] ABSTRACT

In a pressure meter catheter which carries a pressure sensor in its measuring tip a reference pressure is admitted to effect zero setting in accordance with the invention while the instrument is in situ during a measurement, the reference pressure permitting adjustment of an evaluating unit at a remote location. Preferably, the measuring tip is surrounded in sealing fashion by a balloon which can be inflated through the line in the catheter tube through which atmospheric pressure is applied to the sensor as reference pressure for the measurement. Thus the same pressure is available both at the measuring connection and at the reference connection of the sensor, and the pressure differential measured by the sensor consequently is exactly zero.

6 Claims, 2 Drawing Sheets

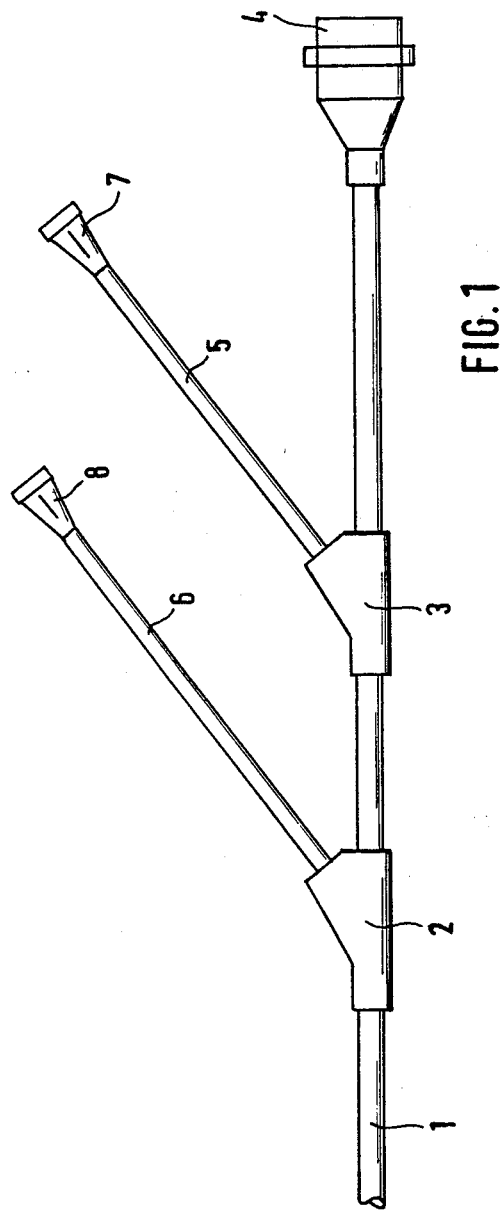

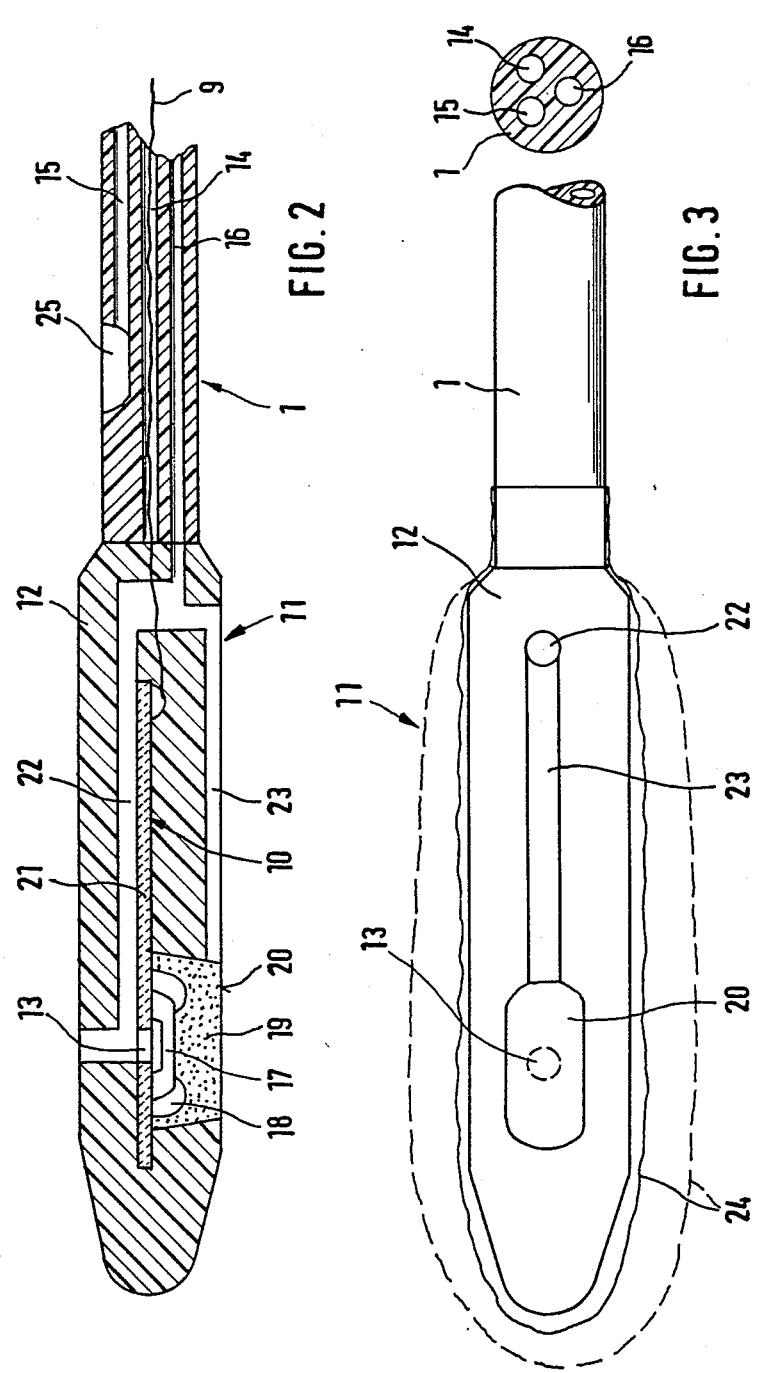

PRESSURE METER CATHETER WITH IN-SITU ZERO SETTING

FIELD OF THE INVENTION

The instant invention relates to a pressure meter catheter having in-situ zero setting, comprising pressure sensor which is disposed at the measuring tip of the instrument to be introduced into a body cavity to be examined and which is connected to an evaluating, indicating, and/or recording means outside the body cavity, a comparison being made with a reference pressure value during the zero setting. The invention also relates to a pressure meter catheter which comprises the following features: a hollow catheter tube whose lumen is open towards both ends, a measuring tip disposed at the proximal end thereof, and a pressure sensor housed in said tip and having a reference connection connected to a reference pressure and communicating with the lumen, and a measured pressure connection connected in pressure transmitting manner, preferably by a membrane to the outer surface of the measuring tip, as well as connecting cables extending through the catheter tube to the distal end thereof.

BACKGROUND OF THE INVENTION

In obstetrics as well as in research a pressure meter catheter is introduced through the cervix into the uterus for close labor monitoring. The instrument detects any pressure variation occurring as to its change and relative magnitude (with respect to the ambient pressure outside of the uterus) and converts it into signals which are applied to a visual display unit for display and, if desired, to a recording apparatus for registration.

As with any sensor use, calibration is a fundamental requirement to be met prior to putting the pressure meter catheter to practical use so as to compensate, at least at a test point, the internal mistakes inherent in the system and possibly also external ones caused by marginal conditions.

In principle, this calibration could be made at any suitable pressure. However, as a rule, ambient pressure (atmospheric pressure) is preferred at which the relative pressure to be measured is zero. In this context, therefore, we do not speak simply of calibration but instead of zero setting. To accomplish that, the ambient pressure is taken as the reference or standard pressure, and the difference, indicated or recorded, from the measured pressure taken by the pressure meter catheter is adjusted to zero by manipulating the display or recording means.

There are two types of catheters for measuring pressure: With the first one, the pressure prevailing in the uterus is transmitted by a liquid column carried in a tube from a proximal measuring point which is isolated by a membrane to a distal pressure sensor which represents the signal transmitter of the measuring arrangement.

If designed properly, the pressure sensor can be disengaged readily from the pressure meter catheter even when the latter is in situ so that the zero setting of the sensor can be effected any time. Apart from a number of disadvantages which are less relevant in the present context, such a pressure meter catheter has the important disadvantages that bubbles in the pressure transmitting liquid have an attenuating and, therefore, falsifying effect and that the hydrostatic measuring error resulting from the vertical difference between the proximal measuring tip and the pressure sensor can be estimated only roughly because the exact location of the measuring tip either is unknown or changes as the patient's body moves.

Therefore, a pressure meter catheter of a second type was proposed to overcome those disadvantages. With this type, the pressure sensor is not located at the distal end of the catheter tube but instead at the proximal end thereof, exactly where the measuring location is. A pressure meter catheter of this kind is sold, for instance, under the name of "INTRAN" by the Utah Medical Products, Inc.

It may be gathered from the instructions for use published by the company for their pressure meter catheter that the zero setting is realized before introducing the catheter as long as its measuring tip is exposed to ambient atmospheric pressure. Furthermore, it is explained in the instructions for use that renewed zero setting is not required once the measuring tip is in situ.

That, however, is true only as long as there are no disturbances. Yet if the displaying or recording unit should fail due to an operating fault or equipment failure during a measurement which may last several hours (e.g. for reasons of inadvertent disconnection of a mains cable when connecting another instrument) then a new zero setting is indispensable. To do that, the measuring tip of the catheter would have to be exposed once more to the ambient air in order to be subjected to atmospheric pressure. Of course, following such a procedure, the measuring tip no longer would be sterile. For this reason another, sterile pressure meter catheter is subjected to zero setting under sterile conditions and is introduced into the cervix upon removal of the former catheter. It need not be explained in detail that any such procedure is cumbersome and expensive, all the more so as it may prove to be necessary when the course of the parturition being monitored takes a rapid and often dramatic turn so that any manipulating of a catheter may be greatly disturbing.

It is another disadvantage of the known catheter that the sterile packing enveloping the catheter must be opened for zero setting so that the catheter is exposed at least in part during the zero setting and, therefore, subject to contamination which gives rise to another problem of sterility.

A pressure meter catheter of the kind mentioned is applied not only in human medicine and obstetrics but also wherever the occurrence of considerable pressures in body cavities of human beings and animals permitting access of pressure sensors is to be monitored, examples being the cud of a ruminant or blood streams.

SUMMARY OF THE INVENTION

In view of these problems it is an object of the invention to find a procedure at least for the renewed zero setting of a pressure meter catheter which carries a pressure sensor at its measuring tip, while the latter is in situ. It is another object of the invention to find a pressure meter catheter which permits such a procedure to be taken. Preferably any zero setting is to be possible and not to be undertaken until the measuring tip is in situ.

This object is met in that either the reference pressure is applied from outside to the pressure sensor while it is inside the body cavity or a reference pressure value is compared with the output of the pressure sensor. In other words, either the output of the pressure sensor in situ is compared with a representative reference value, or a reference pressure is applied to the pressure sensor itself.

In the first case successive storing is possible of the measuring results of the pressure meter catheter. For example, if renewed zero setting is required upon failure of a monitor and replacement thereof by another functioning monitor, a computer may be drawn upon to calculate a simulated reference pressure value on the basis of the memorized measuring data available and possibly based on a given program. This reference pressure value may then be compared for zero setting with the actual pressure value measured.

In the first case it would also be possible, for instance, to fill the catheter tube in the known manner described above with a pressure transmitting liquid and to provide it at its distal end with another previously gauged pressure sensor whose measured value will then provide the reference pressure value for adjustment of the pressure sensor mounted in the measuring tip. In this case, of course, pressure transmission would have to be assured from the outside of the measuring tip to the pressure transmitting liquid.

With this embodiment of the method according to the invention the first zero setting required before activation of the pressure meter catheter may be accomplished also when the pressure meter catheter already has been introduced. In that event the fundamental disadvantages of a catheter with pressure transmitting liquid must be put up with only for the zero setting but not for continuous operation.

In the second case according to the invention a defined reference pressure is generated and applied to the pressure sensor, such as by a passage in the catheter tube. This reference pressure may be applied to the pressure sensor instead of the pressure prevailing in the uterus and may be used as the basis for the zero setting, either as absolute pressure or in relation to a reference pressure which is used continually during the measurement. The pressure meter catheter makes use of this principle and comprises a pressure sensor provided with a measured pressure connection communicating in pressure transmitting manner with the outside of the measuring tip and further provided with a reference connection communicating through a lumen in the catheter tube with the distal end thereof and thus with a reference pressure source which usually is presented by the ambient air in the case of such a catheter.

According to the invention a means for generating a reference pressure is adapted to be connected to the measured pressure connection while the latter is uncoupled from its pressure transmitting connection to the outer side of the measuring tip. In this state, therefore, either a defined pressure gradient prevails between the measured pressure connection of the pressure sensor and its reference connection, if the pressures at the two connections differ or, preferably, there is no pressure gradient if both pressures are the same, as would be the case if the two connections of the pressure sensor both communicated with the same pressure, which can be the ambient air.

That might be the case, for example, if the membrane covering the measured pressure connection of the pressure sensor towards the outside of the measuring tip were lifted off the same by a mechanism, such as a rope controlled cam lever so that coupling would be interrupted with the pressure prevailing at the outside of the membrane.

In that event a separate passage formed in the catheter tube may be provided for the reference pressure and have its proximal end communicate with the measured pressure connection.

It is especially preferred, however, that the means for generating the reference pressure opens into a fluid flow connection arranged between the measured pressure connection and the membrane which covers the same towards the outside. In this manner the membrane is lifted off the measured pressure connection and pressure transmission from the outside of the measuring tip to the pressure sensor is cut off if the reference pressure exceeds the pressure prevailing outside the measuring tip and thus outside the membrane.

A liquid may be used to produce the reference pressure. Yet according to a modification of the invention the means for generating the reference pressure preferably is designed as an air compressor because the pressurized air blown in between the membrane and the pressure sensor leaves no residues there once the zero setting has been terminated so that the further measuring operation is not impaired. This is especially advantageous if the sensor and the membrane are not connected directly but instead only indirectly, such as by a silicone gel pad which protects the pressure sensor from rough mechanical stresses when the catheter is being introduced. A particular advantage of the modification according to the invention resides in the fact that when assembling or introducing the catheter the membrane can be displaced laterally with respect to the protective pad mentioned, thereby constantly applying shearing forces which falsify the measured values on the protective pad and consequently on the pressure sensor. By virtue of the modification of the invention the lift-off of the membrane from the protective pad assures that all the elements involved in the transmission of the measured pressure can adopt their starting position before the measuring begins. At the same time, the zero setting takes place when the catheter already has been introduced.

In view of the fact that the zero setting of the display or recording means takes only very little time, the reference pressure need be maintained for a very short period only, whereby the amount of air supplied to the measuring tip is small. This is important as contaminated air might get into the uterus if the measuring tip were not tight. To avoid that, it is proposed that the air compressor be designed as a piston syringe. The syringe can be sterilized when already drawn up, or it can be sterilized and packed in this state together with the catheter according to the invention so that only sterile air and, in any case, only little air will get into the measuring tip during the zero setting.

For any later renewed zero setting the syringe may be replaced by a new one filled with sterile air.

The reference pressure may be determined by a separate, properly adjusted pressure sensor and compared with the standard pressure which, as a rule, is the atmospheric pressure. In accordance with the preferred modification the reference connection of the pressure sensor communicates with the fluid flow connection for the reference pressure whereby the pressure sensor is pressurized by the same pressure at both connections when the membrane is lifted off. As the differential pressure between the two connections of the pressure sensor becomes zero, the zero setting can be made directly and without any further comparison.

The connecting passage which connects the reference connection with the means for generating the reference pressure which means is connected to the measured pressure connection of the pressure sensor, when in the zero setting mode, may be located at the distal end of the catheter and be opened only, for instance, when zero setting is effected.

According to a preferred modification of the invention the connecting passage is formed in the measuring tip. During zero setting the pressures at either end of the pressure sensor must be balanced. As the zero setting takes place very rapidly, it might happen that the pressure balance is not yet completed at the end of the zero setting if it were taking place through the open hollow and an additional pressure line in the catheter tube. The connecting passage in the measuring tip, however, assures practically instantaneous pressure equalization. In this manner the zero setting becomes simpler still and even more accurate.

With this embodiment, too, a separate pressure line might be provided in the catheter tube. According to a preferred modification, the lumen in the catheter tube, required anyway for the reference pressure, takes the place of a separate pressure line. During zero setting the column of sterile air in the open hollow is simply compressed or displaced by the piston syringe; additional air which first would have to be sterilized is not admitted to the measuring tip. This makes it possible to increase the interior pressure in the measuring tip several times in a row for zero setting by operating the piston syringe. And yet no contaminated air is pumped through the measuring tip so that possible infections are excluded if there should be a leak.

The membrane may be mounted in a window in the measuring tip. But in a preferred modification the membrane is embodied by a balloon which surrounds the measuring tip and, when at rest, lies against the measuring tip and also against the pressure sensor, either directly or indirectly through a compressible pad. This small balloon is inflatable from the distal end of the catheter, for instance, by a piston syringe causing it to be lifted off the pressure sensor. It is a particular advantage of this design of the membrane as a balloon that even at vigorous or excessive pressurization of the measuring tip by the reference pressure which might damage or blow out a membrane set in a window frame, the tightness of the measuring tip remains intact because the balloon, although it bulges sufficiently away from the pressure sensor even when pressurized by a small quantity of air, still can take up a much greater amount of air. Reference pressure is admitted to the interior of the balloon through an aperture which opens into the outer surface of the measuring tip surrounded by the balloon and communicates in the interior of the measuring tip with the lumen of the catheter tube.

This aperture is embodied by a slot bordering on the measured pressure connection of the pressure sensor. Hereby, that part of the balloon opposite the measured pressure connection is the first to receive compressed air and consequently is blown up to arch away from the pressure sensor.

The pressure sensor preferably is designed as a strain gauge, the balloon preferably is made of a high resiliency elastomer, the remaining components of the pressure meter catheter according to the invention are made of physiologically compatible plastics inasmuch as they get into contact with the body to be examined.

Apart from the lumen which may be a simple passage, the catheter tube preferably also comprises a channel for electrical cables and another channel or passage which is open to the outside of the catheter tube at a location near the balloon and serves for introduction of therapeutic liquid into the uterus or withdrawal of liquid samples while the measuring tip is in situ.

BRIEF DESCRIPTION OF THE DRAWING

The invention will be described further, by way of example, with reference to the accompanying drawings, in which:

FIG. 1 is a view of the distal end of an embodiment of a pressure meter catheter according to the invention;

FIG. 2 shows the proximal end of the measuring tip of the embodiment according to FIG. 1 in longitudinal section and on an enlarged scale;

FIG. 3 is a top plan view of the measuring tip shown in FIG. 2 and also indicates the cross section of the catheter tube.

DESCRIPTION OF THE PREFERRED EMBODIMENT

FIG. 1 is an elevational view, almost natural scale, of the distal end of a pressure meter catheter according to the invention for measuring the intrauterine pressure. It shows an end portion of the catheter tube 1, a first branch-off piece 2 where an infusion hose 6 branches off from the multi-channel catheter tube 1, and a second branch-off piece 3 from which an air hose 5 branches off from the catheter tube 1. The end of the catheter tube 1 opens into an electrical coupling 4 suitable for connection to the input cable (not shown) of a monitor or oscillograph (not shown) or the like.

A syringe coupling 8 is fitted at the end of the infusion hose 6 to be joined to a syringe, a mechanical syringe dosing means, or drop infusion equipment (not shown). The free end of the air hose 5, on the other hand, is fitted with a syringe coupling 7 for connection to an air-filled syringe (not shown). In normal operation the syringe coupling 7 remains open.

The air hose 5 is connected to an air passage 16 in the catheter tube 1 (see FIGS. 2 and 3), the infusion hose 6 is connected to an infusion passage 15, and the electrical coupling 4 is mounted at the end of cable passage 14 through which pass the electrical connecting cables 9 starting at a pressure sensor 10 (FIG. 2).

As shown in FIGS. 2 and 3, a measuring tip 11 is fitted at the proximal end of the catheter tube 1. It is formed by a carrier 12 made of plastics and taking up the other component parts as yet to be described. Like the tubes or hoses 1, 5, and 6 it is made of polyethylene or polypropylene.

The pressure sensor 10 comprises an elongated ceramic carrier 21 which is embedded in the carrier 12 and to the end of which facing the catheter tube 1 the electrical cables 9 are connected. At the other end of the ceramic carrier 21 a through aperture 13 is left open. A cup-shaped strain gauge 17 seals this aperture at one side of the ceramic carrier 21, being the lower side in FIG. 2. When a pressure differential occurs between the through aperture 13 and the lower side of the strain gauge 17, for example low pressure, the strain gauge curves, upwardly in the present case, thereby changing its electrical resistance or its electrical capacity and emitting a signal.

The strain gauge 17 is fitted in a recess 18 of the carrier 12 largely filled with a protective pad 19 of silicone gel and behaving like a liquid for pressure transmission to the strain gauge 17. On the other hand, however, it absorbs punctiform loading which otherwise might damage the strain gauge 17.

The external end face of the protective pad 19 which is flush with the outer surface of the carrier 12, presents the measured pressure connection of the pressure sensor 10, while the through aperture 13 is the reference connection thereof.

An equalization space 22 is left free inside the carrier 12 to connect the through aperture 13 with the closest external surface of the carrier 12 and with the air passage 16 in the catheter tube 1. This equalization space 22 further communicates with a longitudinal slot 23 extending almost throughout the length of the carrier 12 and terminating near the measured pressure connection 20.

As shown in FIG. 3, a balloon 24 closely surrounding the carrier 12 is slid over the same and fixed in sealing fashion at the proximal end of the catheter tube 1.

When not pressurized, the balloon adopts the position shown in continuous lines in FIG. 3. In this position the balloon 24 in particular lies against the measured pressure connection 20, functioning as a pressure transmitting membrane.

In blown up state, which will be explained in greater detail below, the balloon adopts the position shown in discontinuous lines in FIG. 3 in which position it is lifted off the measured pressure connection 20.

As the balloon 24 is made of silicone rubber which is at least somewhat transparent, the measured pressure connection 20 and the slot 23 are visible in FIG. 3.

FIG. 2 further shows an infusion aperture 25 formed in the wall of the catheter tube 1 near the proximal end thereof and presenting an outlet of the infusion passage 15.

The pressure meter catheter shown is destined for one-time use and is welded in sterile condition in a sheath which is not permeable to bacteria. The syringe couplings 7 and 8 may be closed by removable plugs. A drawn-up disposable syringe filled with air likewise may be coupled detachably to the syringe coupling 7 for the air hose 5.

For use, the catheter having been taken out of its sterile packing is introduced at once by its measuring tip 11 through a patient's cervix into her uterus where its positioning may be effected under ultrasonic control, if desired. If necessary, the catheter tube 1 is fixed at the patient.

Thereupon the catheter is connected by its electrical coupling 4 to a monitor or plotter or the like. Then the piston of the air-filled syringe which was connected from the beginning or has been coupled in the meantime is pressed down slowly and completely. Towards the end of this procedure the zero-set button of the monitoring or recording apparatus mentioned is pushed, or the zero setting is effected in any other mode provided for. Subsequently, the piston syringe is detached from the syringe coupling 7 and removed.

As the piston of the syringe is depressed the pressure in the air passage 16 rises sharply, passing through the equalization space 22 in the measuring tip 11 and its connecting apertures to the outside of the carrier 12 and thus into the interior of the balloon 24 which is blown up by it, as shown in discontinuous lines in FIG. 3. The uniform air pressure prevailing inside the balloon is applied both to the measured pressure connection 20 and to the reference connection 13. Consequently, the strain gauge 17 is subjected to a pressure differential of zero magnitude. During this time the downstream display or recording apparatus is adjusted; the display now must show a relative pressure of zero value.

Upon removal of the syringe from the coupling 7 the pressure in the air passage 16 and consequently also the pressure inside the balloon 24 drops until the air pressure at the reference connection 13, in the air passage 16, and in the air hose 5 corresponds to atmospheric pressure and the balloon 24 closely engages the external surface of the carrier 12.

If subsequent pressure adjustment is required, for example, because the course of the pressure so far shown only on a screen is to be recorded as well by additional equipment, then an air-filled, drawn-up syringe is connected to the coupling 7, and the zero setting described above is repeated once more.

This means that the zero setting may be undertaken as many times as required, while the measuring tip 11 of the catheter remains in place from the very beginning. The risk of infection thus is reduced to the minimum and, at the same time, very accurate measurements can be achieved as the single variable disturbing factor which appears during the measurement is the static liquid pressure in the interior of the uterus.

What is claimed is:

1. A pressure meter catheter comprising:
   a hollow catheter tube whose lumen is open at both ends;
   a fitting adapted to receive a gas pressure source connected to said lumen at or near one of said ends;
   a measuring tip disposed at the other end, the measuring tip comprising:
   a measuring tip body having a cavity,
   a first opening at said measuring tip body, at which opening said cavity is connected with the lumen of said catheter tube,
   a second opening at said measuring tip body open to the outside thereof,
   an inflatable balloon, closely covering the outside of said measuring tip body and sealingly covering the second opening, a third opening in said measuring tip body connecting the inside of said balloon with the cavity of said measuring tip body,
   a strain gauge, positioned on a support and sealingly covering a through bore in that support, which bore connects said cavity of said measuring tip body with said second opening, and being connected to electric measuring leads which pass through said catheter tube, said strain gauge sensing the difference between the pressure in the inside of said cavity and at the outside of said balloon,
   said strain gauge being in a position of zero adjustment when said balloon is inflated by means of a gas pressure source.

2. The pressure meter catheter of claim 1 wherein a pressure transmitting protecting pad is disposed in a recess in said measuring tip body between said strain gauge and the inside of said balloon, the recess forming said second opening, and said measuring tip body having a longitudinal slot connected with said cavity and ending near said recess.

3. The pressure meter catheter of claim 1 or 2, wherein an injection syringe is connected to said catheter tube at said fitting to provide a gas pressure source.

4. The pressure meter catheter of claim 3, wherein said injection syringe is removably disposed.

5. The pressure meter catheter of claim 4, wherein said injection syringe is adapted to be filled with sterilized air.

6. The pressure meter catheter of claim 3, wherein said injection syringe is adapted to be filled with sterilized air.

* * * * *